(12) United States Patent
Gopal

(10) Patent No.: US 10,745,351 B2
(45) Date of Patent: Aug. 18, 2020

(54) METHOD OF PRODUCING PHYCOCYANIN POWDER

(71) Applicant: WELLISEN NUTRACEUTICALS PVT. LTD., Nanjangud (IN)

(72) Inventor: K. M. Gopal, Nanjangud (IN)

(73) Assignee: Wellisen Nutracenticals PVT, LTD, Nanjangud (IN)

(*) Notice: Subject to any disclaimer, the term of this patent is extended or adjusted under 35 U.S.C. 154(b) by 0 days.

(21) Appl. No.: 16/123,476

(22) Filed: Sep. 6, 2018

(65) Prior Publication Data

US 2019/0084930 A1 Mar. 21, 2019

Related U.S. Application Data

(60) Provisional application No. 62/560,339, filed on Sep. 19, 2017.

(51) Int. Cl.
| | | |
|---|---|---|
| *C07D 207/44* | (2006.01) | |
| *A23L 33/135* | (2016.01) | |
| *C12P 17/16* | (2006.01) | |
| *C12N 1/12* | (2006.01) | |
| *A23L 33/105* | (2016.01) | |
| *A23L 29/00* | (2016.01) | |

(52) U.S. Cl.
CPC .......... *C07D 207/44* (2013.01); *A23L 29/045* (2016.08); *A23L 33/105* (2016.08); *A23L 33/135* (2016.08); *C12N 1/12* (2013.01); *C12P 17/165* (2013.01); *A23V 2002/00* (2013.01)

(58) Field of Classification Search
CPC .............. A61K 2300/00; A61K 31/715; A61K 31/726; A61K 31/736; A61K 31/409; A61K 45/06; A61K 31/122; A61K 31/202; A61K 31/685; A61K 31/7028; A61K 31/728; A61K 35/16; A61K 35/612; A61K 36/02; A61K 36/05; A61K 36/06; A61K 36/185; A61K 36/324; A61K 36/74; A61K 36/9066; A23V 2002/00; A23V 2200/04; A23V 2200/044; A23V 2250/184; A23V 2250/20; A23V 2250/202; A23V 2200/316; A23V 2250/1842; A23V 2250/187; A23V 2250/1882; C07H 21/00; C07H 1/08; Y10S 977/853; A01N 65/03; A01N 25/16; A01N 25/34; A01N 25/10; A01N 25/30; A23L 2/58; A23L 33/105; A23L 33/135; A23L 5/40; A23L 5/44; A23L 29/045; A23L 29/10; A23L 29/212; A23L 29/37; A23L 5/46; A23L 33/115; A23L 33/12; C08B 37/006; A23D 9/00; A23D 9/013; C07D 207/44; C08J 2205/06; C08J 2405/00; C08J 2201/024; C08J 2201/026; C08J 2201/03; C08J 2203/04; C08J 2205/05; C08J 2205/052; C08J 2205/10; C08J 2207/00; C08J 2311/00; C08J 2323/08; C08J 2331/04; C08J 2375/04; C08J 3/22; C08J 9/0023; C08J 9/0033; C08J 9/0061; C08J 9/0066; C08J 9/009; C08J 9/103; C12P 17/165; C12P 23/00; C12P 7/26; A43B 13/04; A43B 17/006; A43B 17/10; A43B 17/14; A43B 1/00; A43B 1/0045; A43B 1/02; A43B 5/0486; C08L 2201/02; C08L 2310/00; C08L 5/00; C09B 61/00; C12N 1/12; C12N 1/06; C12N 9/20; C12N 9/2488; D01D 5/08; D01F 1/103; D03D 17/00; D06M 15/03; D06M 16/00; D06M 2101/06; D06M 23/08; D06M 2400/01; D06P 1/48; D10B 2201/01; D10B 2331/10; D10B 2401/10; A23K 10/12; A23K 10/16; A23K 10/30; A23K 20/142; A23K 20/158; A23K 20/174; A23K 50/30; A23K 50/75; A23K 50/80; A61L 2400/12; A61L 27/34; A61L 27/50
See application file for complete search history.

(56) References Cited

U.S. PATENT DOCUMENTS

| | | | |
|---|---|---|---|
| 8,563,701 | B2 | 10/2013 | Ehmann et al. |
| 9,131,724 | B2 | 9/2015 | Ehmann et al. |
| 9,238,043 | B2 * | 1/2016 | Minatelli ........... A61K 36/9066 |
| 10,195,585 | B2 * | 2/2019 | Soni ...................... B01J 23/883 |
| 2005/0220498 | A1 | 10/2005 | Han et al. |

(Continued)

*Primary Examiner* — Deborah K Ware
(74) *Attorney, Agent, or Firm* — Gipple & Hale; John S. Hale

(57) ABSTRACT

A process for providing phycocyanin from a blue-green algae biomass comprising the steps of forming a slurry of blue-green algae by mechanically mixing the blue-green algae in water to break up filaments of the biomass and incubating the macerated slurry in a container with at least a 1% flocculating agent for a period of time sufficient to separate a blue extract from the slurry. The blue extract is separated and filtered through a filter to obtain a blue filtrate and the blue filtrate is mixed in a container with an ammonium sulfate precipitate for a suitable period of time to obtain supernatant protein separation. The supernatant is syphoned from the container and the settled participate is centrifuged at a rpm ranging from about 3500 rpm to about 4500 rpm for a sufficient time to produce phycocyanin precipitate. The phycocyanin precipitate is spray dried to form a phycocyanin powder which is collected and purified with a citrate and water mixture to obtain a supernatant and phycocyanin residue with the phycocyanin residue being redissolved in water and sprayed to dry into a phycocyanin powder.

21 Claims, 1 Drawing Sheet

(56) References Cited

U.S. PATENT DOCUMENTS

| | | | | |
|---|---|---|---|---|
| 2007/0082008 A1* | 4/2007 | Harel | .................... | A23K 20/142 |
| | | | | 424/195.16 |
| 2013/0344576 A1* | 12/2013 | Milos | ....................... | C12N 1/06 |
| | | | | 435/271 |
| 2014/0045217 A1* | 2/2014 | Milos | ....................... | C12N 1/06 |
| | | | | 435/71.1 |
| 2016/0130627 A1* | 5/2016 | Milos | ....................... | C12N 1/06 |
| | | | | 435/257.1 |
| 2017/0027168 A1* | 2/2017 | Heath | .................... | A01N 25/30 |

* cited by examiner

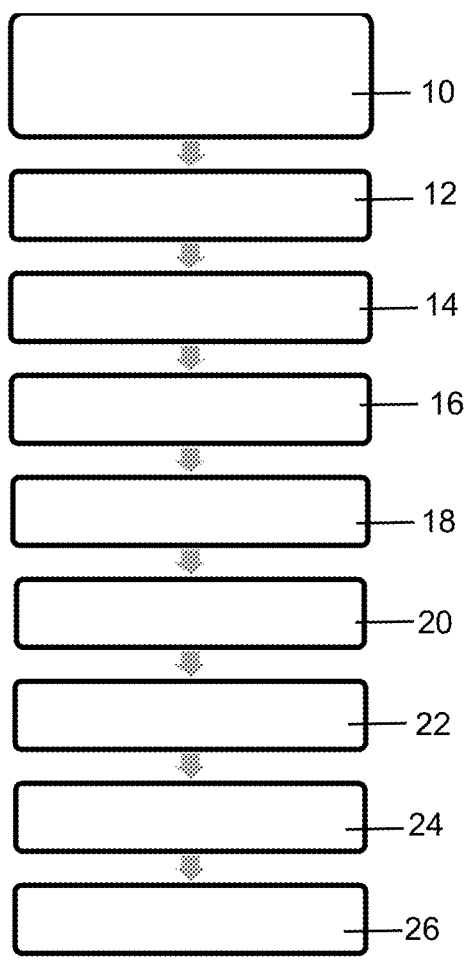

METHOD OF PRODUCING PHYCOCYANIN POWDER

RELATED APPLICATIONS

This is a utility patent application claiming priority and benefit from U.S. Provisional Patent Application No. 62/560,339 filed Sep. 19, 2017.

STATEMENT REGARDING FEDERALLY SPONSORED RESEARCH OR DEVELOPMENT

Not applicable.

REFERENCE TO SEQUENCE LISTING, A TABLE OR A COMPUTER PROGRAM LISTING COMPACT DISC APPENDIX

None.

BACKGROUND OF THE INVENTION

1. Field of Invention

The present invention is directed to a method of harvesting phycocyanins from blue-green algae and concentrating the phycocyanin.

2. Description of the Prior Art

Blue-green algae, a cyanobacteria, forms a life-supporting foundation in the natural food chain by providing the essential vitamins, minerals, proteins, and nutrients required to support life. The health benefits of certain algae have long been appreciated when used as a dietary supplement for promoting and sustaining human health.

Cyanobacteria are widely used in aquaculture for phycocyanin production. Among the cyanobacteria, the genus *Arthrospira* (formerly known as *Spirulina* and still commercially known as *Spirulina'*) is the most commonly cultured genus; however, phycocyanin has been extracted from other genera such as *Aphanizomenon* and *Anabaena*. The main species in culture for the production of phycocyanin are *Arthrospira platensis* and *Arthrospira maxima*. These are both filamentous cyanobacteria with spiral-shaped filaments or trichomes.

Phycocyanin, an accessory pigment to chlorophyll, is a pigment protein (phycobiliprotein) having a characteristic blue color and is mainly found in cyanobacteria.

Phycocyanin is a water soluble protein with stability over a large pH range and is one of the main pigments of cyanobacteria as for example *spirulina* (*Arthrospira platensis, Arthrospira* maxima) or AFA (*Aphanizomenon* Flos-Aquae). At rest, phycocyanin has a blue color and a red fluorescence. It has a maximum light absorption at 620 nm (ranging from 610 nm to 620 nm) and an emission radiation at 635 nm. This quality makes it a natural fluorescent product which is favored in biomedical diagnostics.

Phycocyanin is a molecule of great interest to the scientific community in particular because of its beneficial properties for human and animal health and wellness. Phycocyanin is consumed in particular for its antioxidant properties and also for its ability to promote the production of stem cells. Phycocyanin has a wide range of applications such as, fluorescent markers, antioxidants, immuno-modulant in pathological conditions, neuroprotective and hepatoprotective, natural pigments in food and cosmetics and the like.

However, phycocyanin is an expensive molecule which is difficult to extract. It is a molecule which is very quickly degraded after extraction and is susceptible to bacterial contamination, which raises the costs because in liquid form (water), this molecule has to be extracted under sterile conditions and packaged in single doses.

Conventional methods for isolating phycocyanin from algae/cyanobacteria involve suspending dried, fresh or frozen blue-green algae in an aqueous solution to produce a cell suspension; disrupting the integrity of the algal/cyanobacterial cells, thereby releasing cytoplasmic contents to produce a disrupted cell suspension; separating solid and liquid phases of the disrupted cell suspension; contacting the liquid phase of the disrupted cell suspension with a non-ionic polyaromatic macroreticular adsorbent resin; collecting the liquid phase from the resin to produce a phycocyanin extract; and optionally dehydrating the phycocyanin extract.

Some processes involve separation and purification of phycocyanin including precipitation, centrifugation, dialysis and chromatography processes. These methods are difficult to carry out and are also expensive, and the resulting purity of the produced phycocyanin is generally not of the desired range/volume.

Though various process for the extraction of phycocyanin are known, the extraction rate of phycocyanin is not high, resulting in an increased production costs with the processes currently used being tedious and time consuming.

It is therefore, desired to provide a simple and economic process which can be an alternative to known processes and which can also overcome the drawbacks associated with known processes by eliminating complex process steps and time consuming process steps all of which produce less yield and are not economically feasible.

A number of prior art patents and publications have discussed the manufacture and processing of phycocyanin from algae.

U.S. Patent Application Publication Number 2005/0220948 published Oct. 6, 2005 discloses suspension of *spirulina* in distilled water to destroy its cell membranes by osmotic treatment so that chromoproprotein phycocyanin leaks out of the cell membranes. The chromoproprotein is denatured by heating, and condensing the resultant mixture under reduced pressure or freeze drying.

U.S. Pat. No. 8,563,701 issued Oct. 22, 2013 is directed to methods for purifying phycocyanin from blue-green algae extracts.

U.S. Pat. No. 9,131,724 issued Sep. 15, 2015 also relates to methods for purifying phycocyanin from blue-green algae extracts.

The present invention overcomes these problems and production deficiencies are solved by this invention in the manner described below.

SUMMARY OF THE INVENTION

The present invention herein disclosed provides for an improved method that can be used for the harvesting of phycocyanins from a blue-green algae biomass. The inventive method results in a significant increase in phycocyanin production levels, having at least a #2 purity or higher and is a clear improvement over the prior art.

The invention is a process for obtaining phycocyanin from a blue-green algae biomass comprising the steps of: forming a slurry 10 of blue-green algae by mechanically mixing the biomass in water to break up filaments of the biomass and incubating the macerated slurry in a container with at least a 1% flocculating agent for a period of time sufficient to separate a blue extract from the slurry. The blue extract is separated and filtered 12 through a filter to obtain a blue extract filtrate. The blue extract filtrate is mixed in a container with an ammonium sulfate precipitate for a suitable period of time to obtain protein separation into a supernatant and settled precipitate 14. The supernatant is syphoned out from the container and the settled precipitate is centrifuged 16 at a high rpm ranging from about 3500 rpm to about 4500 rpm for a sufficient time to produce phycocyanin precipitate. The phycocyanin precipitate is then spray dried 18 to form a phycocyanin powder. The phycocyanin powder is purified 20 with a citrate and water mixture to obtain a supernatant and phycocyanin residue 22. The phycocyanin residue is collected by redissolving the residue in water and spraying 24 the phycocyanin solution on a collector means and analyzing the final product for purity.

Phycocyanins may be used in many applications, including, but not limited to, use as a natural food coloring, as an antioxidant in the food supplement industries, in the nutraceutical, pharmaceutical, and cosmeceutical industries, and as a non-toxic ink.

It is an object of the invention to provide improved methods for the commercial production of phycocyanins.

It is a principal object of this invention is to provide a process for extracting and stabilizing and purifying phycocyanin and its applications in particular in diagnostics and in the medical, food, food supplements or as cosmetics.

These and other objects, advantages, and novel features of the present invention will become apparent when considered with the teachings contained in the detailed disclosure along with the accompanying drawings.

BRIEF DESCRIPTION OF THE DRAWINGS

The present invention will be described with reference to the appended FIGURE, in which:

FIG. 1 is a schematic process diagram illustrating a method for the purification of phycocyanin from aqueous extracts of cyanobacteria.

DESCRIPTION OF THE INVENTION

The present invention is directed towards a method for commercially producing phycocyanin and the preferred embodiment and best mode of the invention is shown in FIG. 1 and previously described in the Summary and described in more detail below.

The term "algae" is the plural form of "alga," which is a cell of a *microalgae* species. The term "blue-green algae" refers to multiple cells of a single *Aphanizomenon* species, multiple cells of a single *Spirulina (Arthrospira)* species, or a mixture of cells from multiple *Aphanizomenon* and/or *Spirulina (Arthrospira)* species.

Blue-green algae is a gram-negative photosynthetic bacteria belonging to the Division Cyanophyta that may exist in unicellular, colonial, or filamentous forms. Representative blue-green algae include, but are not limited to: the *Spirulina (Arthrospira)* species and the *Aphanizomenon* species. *Aphanizomenon* flos aquae (AFA) is another non-limiting type of blue-green algae which can be used.

As previously noted, phycocyanin is an expensive molecule which is difficult to extract. It is further a molecule which is very quickly degraded, after extraction, and is subject to bacterial contamination. These differences raise the costs because in liquid form (water), this molecule has to be extracted under sterile conditions and packaged in single doses.

In *Spirulina (Arthrospira)* algae both *platensis* and maxima, one of the accessory photosynthetic pigments are phycobiliproteins, which form an extremely efficient transfer chain in photosynthesis. *Spirulina* algae which were used in the inventive process were, was cultivated in a modified Zarrouk's medium which changes the phosphorus nutrient ($K_2$ $HPO_4$-Dipotassium hydrogen phosphate) to phosphoric acid $H_3 PO_4$.

The composition of the modified Zarrouk's Medium is as follows in Table 1:

TABLE 1

| Nutrients | Quantity per liter of water |
| --- | --- |
| $NAHCO_3$ (Sodium bicarbonate) | 16.8 g |
| $K_2HPO_4$ (Dipotassium hydrogen phosphate)/Phosphoric acid = $H_3PO_4$) | 0.5 g/0.31 g |
| $NaNO_3$ (Sodium nitrate) | 2.5 g |
| $K_2SO_4$ (Potassium Sulfate) | 1.0 g |
| $MgSO_4 \cdot 7 H_2O$ (Magnesium sulfate) | 0.20 g |
| $CaCl_2$ (calcium chloride) | 0.04 g |
| $FeSO_4 \cdot 7 H_2O$ (Ferrous sulfate) | 0.01 g |
| EDTA (ethylene diamino tetracetic acid) | 0.08 |

The algae culture growth was maintained at 600 mg/L to 800 mg/and pH was maintained at 10 to 11.0. The climatic condition varied from season to season. In summer, culture temperature was maximum 34° C. and in winter the culture temperature was minimum 19° C.

The base flow chart for the inventive phycocyanin producing process is shown in FIG. 1.

In an embodiment of the present disclosure, the process of producing phycocyanin powder from a blue-green algae biomass comprises the steps of:

a. harvesting blue-green algae biomass or culture by flocculation followed by filtration;

b. washing the harvested biomass (slurry) 10 with water to remove adhering chemicals to obtain a neutral pH of the slurry;

c. breaking up the filaments of the algae biomass to release cytoplasmic contents with mechanism treatment such as churning with a screw pump and grinding machine at 2800 rpm to breakup cells/filaments of *spirulina;* d. incubating the macerated slurry in a container for about 14 to about 18 hours with a 1% flocculating agent or agents at room temperature;

e. separating the blue extract located at the bottom of the container after incubation and discarding the remaining debris;

f. filtering 12 the blue extract obtained in paragraph e. through a #500 mesh cloth followed by filtration through a satin cloth to obtain a blue extract filtrate;

g. mixing the blue extract filtrate with ammonium sulfate precipitates having a 30% (vol/wt.) in a container for a period ranging from 8 hours to 30 hours with the preferred time being about 8 hours or a sufficient time to obtain protein separation and concentration 14 in a container;

h. syphoning out the supernatant from the top of the container and centrifuging 16 the settled blue precipitate in a range of about 3500 rpm to about 4500 rpm with the preferred speed being at about 3500 rpm for about 15 minutes;

i. spray drying 18 the centrifuged blue precipitate at 170° C. (inlet temperature with an outlet temperatures ranging from about 55° C. to about 65° C.) using a atomist type or spray drier to form a powder with a solid content of 25% to 40%;

j. collecting the spray dried phycocyanin powder and testing the phycocyanin powder for water solubility; the output color being blue in color since it contains the precipitate chemical (ammonium sulfate), for further purification;

k. purifying 20 the collected powder with a citrate and water mixture. The preferred purification mixture formula/solution used is: 1 part by weight of collected phycocyanin powder, 2 parts by weight Trisodium citrate and 8 parts by weight water.

l. mixing the formula of step k. in a reactor or mixing vessel for about 20 minutes to about 60 minutes with a preferred mixing time of 30 minutes at room temperature and filtering 22 the mixture on satin cloth or centrifuge the mixture at a range of about 3800 rpm to about 5000 rpm, preferably 4000 rpm for about 15 to about 30 minutes;

m. allowing the mixture to settle for about 3 hours to about 24 hours, preferably and 3 hours at room temperature to separate.

n. discarding the supernatant or filtrate from the settled separated mixture. The residue is re-dissolved in water (re-suspended) and the suspension sprayed with either an atomizer type or concurrent type of spray drier to form dry feed stock. The resuspension was spray dried 24 at 170° C. at the Inlet temperature and 60° C.±5° C. at the outlet temperature. The solid content obtained was about 25% to about 15%. The phycocyanin can be spray dried judiciously. Temperature and solid content of spray drying feed is important to get soluble product;

o. the dried output of dark blue colored product was collected and analyzed 26 to have at least a purity index of 2.0; and p. the final blue colored powder was sifted in #80 mesh to get uniform particle size with about 5% to about 15% by weight being retained by the #80 mesh and was immediately packed in a plastic self-sealing cover and aluminum pouch under sterile conditions. The packaged material is stored at cool & dry condition.

The phycocyanin powder obtained from the above-identified process has the following physical parameters:

Physical parameters:

| a. | Solubility: | 100% in Water |
| b. | Color: | Dark Blue |
| c. | Bulk Density: | 0.2-0.35 g/cc |

The phycocyanin powder obtained from the above-identified process has the following chemical parameters:

| a. | Moisture: | <2% |
| b. | Protein -: | >60% |
| c. | Crude-C-phycocyanin: | >50% |
| d. | Pure-C-phycocyanin: | >25% |
| e. | Purity index A620/280: | >2.0 |

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims.

What is claimed is:

1. A process for providing phycocyanin from a blue-green algae biomass comprising the steps of:
    a) forming a slurry of blue-green algae by mechanically mixing same in water to break up filaments of the biomass;
    b) incubating the macerated slurry in a container with at least a 1% flocculating agent for a period of time sufficient to separate a blue extract from said slurry.
    c) separating the blue extract and filtering it through a filter to obtain a blue extract filtrate;
    d) mixing the blue extract filtrate in a container with an ammonium sulfate precipitate for a suitable period of time to obtain separation into a supernatant and settled precipitate;
    e) syphoning out the supernatant from said container and centrifuging the settled precipitate at a high rpm ranging from about 3500 rpm to about 4500 rpm for a sufficient time to produce phycocyanin precipitate;
    f) drying the phycocyanin precipitate to form a phycocyanin powder;
    g) purifying the obtained phycocyanin powder to obtain a supernatant and phycocyanin residue; and
    h) collecting the phycocyanin residue and redissolving said phycocyanin residue in water and spraying the phycocyanin solution on a collector means to provide phycocyanin.

2. The process according to claim 1, wherein in step c) said filter is a #500 mesh cloth.

3. The process according to claim 1, wherein in step d) said blue extract filtrate is mixed with said ammonium sulfate for at least 8 hours.

4. The process according to claim 1, wherein in step g) the purification of the obtained phycocyanin powder is with a citrate and water solution.

5. The process according to claim 1, wherein said algae biomass is selected from *Arthrospira platensis* or *Arthrospira maxima*.

6. The process according to claim 1, wherein in step g) said phycocyanin powder is purified to obtain phycocyanin having a purity index of at least 2.0.

7. The process according to claim 1, wherein said algae biomass is selected from the genus *Aphanizomenon*.

8. The process according to claim 1, wherein said algae biomass is selected from a mixture of two or more of *Arthrospira platensis, Arthrospira* maxima and algae of the genus *Aphanizomenon*.

9. The process according to claim 1, wherein said biomass is fresh.

10. The process according to claim 1, wherein said biomass is frozen.

11. The process according to claim 1, wherein said biomass is dried.

12. The process according to claim 1, wherein in step d) the suitable period of time ranges from about 8 hours to about 30 hours.

13. The process according to claim 1, wherein in step e) the sufficient time ranges from about 20 minutes to about 60 minutes.

14. The process according to claim 4, wherein citrate and water solution is comprised of 8 parts water, 2 parts trisodium citrate and 1 part phycocyanin.

15. A process of producing phycocyanin powder comprising the steps of:

a) cultivating a *Spirulina* algae in a medium to obtain a culture;
b) harvesting *Spirulina* culture to obtain a biomass;
c) washing said biomass with water to obtain a slurry with a neutral pH;
d) breaking up the filaments of the *spirulina* biomass with mechanical treatment;
e) incubating the macerated slurry for about 14 to about 18 hours with flocculating agents at room temperature;
f) separating a blue extract from the incubated slurry and discarding the remaining debris;
g) filtering the blue extract to obtain a filtrate;
h) mixing the filtrate with ammonium sulfate precipitates in a container for a time period sufficient to obtain separation of the filtrate into a blue precipitate and a supernatant;
i) syphoning out the supernatant from the container and centrifuging settled blue precipitate at about 3500 rpm for about 15 minutes;
j) drying the blue precipitate at 170° C. to form a phycocyanin powder; and
k) collecting the phycocyanin powder.

16. The process according to claim 15, wherein said mechanical treatment of step d) includes passing said biomass through a screw pump and grinding machine at a speed of about 2800 rpm.

17. The process according to claim 15, wherein said culture is fresh.

18. The process according to claim 15, wherein said culture is frozen.

19. The process according to claim 15, wherein said culture is dried.

20. The process according to claim 15, including an additional step 1) of purifying the collected phycocyanin powder in a citrate and water mixture.

21. A process of producing phycocyanin powder comprising the steps of:
a) washing a *Spirulina* with water to obtain a slurry with a neutral pH;
b) breaking up the filaments of the *Spirulina* biomass with mechanical treatment;
c) incubating the macerated slurry with flocculating agents for a suitable period of time at room temperature to form a blue extract;
d) separating the blue extract and discarding the remaining debris;
e) filtering the blue extract to obtain a filtrate;
f) mixing the filtrate with ammonium sulfate precipitates in a container for a time period sufficient to obtain separation into blue precipitate and a supernatant;
g) draining out the supernatant and centrifuging said blue precipitate; and
h) drying said blue precipitate to form a phycocyanin powder.

* * * * *